(12) United States Patent
Maeno et al.

(10) Patent No.: US 6,507,015 B1
(45) Date of Patent: Jan. 14, 2003

(54) RAINDROP SENSOR HAVING PLANO-CONVEX LENS

(75) Inventors: Satoru Maeno, Kariya (JP); Osamu Terakura, Nagoya (JP)

(73) Assignee: Denso Corporation, Aichi-Pref. (JP)

( * ) Notice: Subject to any disclaimer, the term of this patent is extended or adjusted under 35 U.S.C. 154(b) by 153 days.

(21) Appl. No.: 09/645,620

(22) Filed: Aug. 25, 2000

(30) Foreign Application Priority Data

Aug. 27, 1999 (JP) .......................................... 11-242096

(51) Int. Cl.⁷ ................................................ G02B 6/42
(52) U.S. Cl. ................... 250/227.25; 250/216; 340/602
(58) Field of Search ........................... 250/216, 227.25, 250/574; 318/483; 340/602; 315/76–84

(56) References Cited

U.S. PATENT DOCUMENTS

| | | | |
|---|---|---|---|
| 4,701,613 A | | 10/1987 | Watanabe et al. |
| 5,278,425 A | * | 1/1994 | Bendicks et al. ............ 250/574 |
| 5,323,637 A | * | 6/1994 | Bendicks et al. ........... 73/29.01 |
| 5,391,891 A | | 2/1995 | Wiegleb et al. |
| 5,498,866 A | * | 3/1996 | Bendicks et al. ....... 280/227.25 |
| 5,572,017 A | * | 11/1996 | Veltum et al. .......... 250/227.25 |
| 5,661,303 A | | 8/1997 | Teder |
| 5,898,183 A | * | 4/1999 | Teder ........................... 250/574 |
| 6,232,603 B1 | * | 5/2001 | Nelson ................... 250/339.11 |
| 6,262,407 B1 | * | 7/2001 | Teder ........................... 250/205 |

FOREIGN PATENT DOCUMENTS

WO    WO 98/57830    12/1998

* cited by examiner

Primary Examiner—Stephone B. Allen
Assistant Examiner—Eric J Spears
(74) Attorney, Agent, or Firm—Nixon & Vanderhye PC

(57) ABSTRACT

A raindrop sensor has a prism body, incoming radiation side plano-convex lens portions each provided on inclined surfaces of the prism body for receiving light from light-emitting elements, and outgoing radiation side plano-convex lens portions provided on inclined surfaces of the prism body for emitting light toward a light-receiving element. The plano-convex lens portions are configured to cause a relatively small number of light-receiving element(s) to receive light from a number of outgoing radiation side plano-convex lens portions. Such a raindrop sensor can be made to have a more structure while employing a widened detection region.

10 Claims, 2 Drawing Sheets

RAINDROP SENSOR HAVING PLANO-CONVEX LENS

CROSS REFERENCE TO RELATED APPLICATION

This application is based upon and claims the benefit of Japanese Patent Applications No. 11-242096 filed on Aug. 27, 1999, the contents of which are incorporated herein by reference.

BACKGROUND OF THE INVENTION

1. Field of the Invention

This invention relates to a raindrop sensor suitably used for a vehicle wiper automatic control device.

2. Description of the Related Art

A conventional raindrop sensor is shown in FIG. 4. The raindrop sensor is attached to an interior wall of a vehicle windshield W to optically detect presence of raindrops. In the raindrop sensor, a light-emitting element 2 and a light-receiving element 3 are disposed at both sides in a longitudinal direction of a prism 1. The prism 1 has a plano-convex lens 1a facing the light-emitting element 2, a plano-convex lens 1b facing the light-receiving element 3, and a prism body 1c provided between the lenses 1a and 1b.

The plano-convex lens 1a changes light from the light-emitting element 2 to parallel rays that are to be incident on the prism body 1c. Light incident on the prism body 1c is reflected several times between an exterior wall of the windshield W and the central portion upperwall of the prismbody 1c as indicated by arrows in FIG. 4, and then enters the plano-convex lens 1b. Light from the plano-convex lens 1b converges to be incident on the light-receiving element 3. Incidentally, in FIG. 4, reference numeral 4 denotes a transparent adhesive layer.

In the raindrop sensor having the structure as described above, a light-emitting axis of the light-emitting element 2 and a light-receiving axis of the light-receiving element 3 must be respectively inclined at approximately 45 degrees with respect to the exterior wall of the windshield W to provide the optical path of light as described above. The light-emitting element 2 and the light-receiving element 3 are therefore provided on a wiring board 5 disposed above the prism 1 so that the light-emitting axis and the light-receiving axis have inclination of approximately 45 degrees with respect to the wiring board 5. The prism body 1c has two inclined surfaces on which the convex lenses 1a and 1b are respectively disposed so that optical axes of the convex lenses 1a and 1b respectively correspond to the light-emitting axis and the light-receiving axis of the elements 2 and 3.

In this connection, each of the inclined surfaces of the prism body 1c must have an area sufficient for holding each of the convex lenses 1a and 1b. This may result in unnecessary increase in height or length of the prism 1. In addition, since the light-emitting element 2 and the light-receiving element 3 project downward from the wiring board 5 via leads, the wiring board 5 must be positioned at a much higher position than the prism 1.

Further, when the raindrop sensor has several light-emitting elements to widen a detection region to improve detection accuracy, the raindrop sensor must have several light-receiving elements, a number of which corresponds to that of the light-emitting elements.

SUMMARY OF THE INVENTION

The present invention has been made in view of the above problems. An object of the present invention is to provide a raindrop sensor constructed with a compact structure with a decreased number of parts and having a widened detection region.

According to the present invention, briefly, a raindrop sensor has first and second light-emitting elements and first a and second incoming radiation side plano-convex lens portions provided on a prismbody to face the first and second light-emitting elements. The raindrop sensor further has a light-receiving element and first and second outgoing radiation side plano-convex lens portions. The first and second outgoing radiation side plano-convex lens portions are provided by dividing one, plano-convex lens into two pieces so that each of the first and second outgoing radiation side plano-convex lens portions has a divided surface. The divided surface of the first outgoing radiation side plano-convex lens portion faces the divided surface of the second outgoing radiation side plano-convex lens portion.

Accordingly, when the raindrop sensor is attached to a windshield, light emitted by the first and second light-emitting elements is incident on a wide region of an exterior wall of the windshield after passing through the first and second incoming radiation side plano-convex lens portions, and is reflected by the exterior wall. Then, light enters the first and second outgoing radiation side plano-convex lens portions, and is refracted toward the divided surface by each of the first and second outgoing radiation side plano-convex lens portions. As a result, light from both the first and second outgoing radiation side plano-convex lens portions can enter the light-receiving element.

The number of the light-receiving elements can be decreased largely as compared to that of the light-emitting element(s). As a result, the number of parts for the raindrop sensor is reduced. Since the outgoing radiation side lens portions are provided by dividing the one plano-convex lens, the size of the prism body for holding the lens portions can be reduced in a vertical direction. As a result, a gap between the prism body and a wiring board holding the light-emitting and light-receiving elements can be reduced resulting in decreases in height and length of the raindrop sensor.

BRIEF DESCRIPTION OF THE DRAWINGS

Other objects and features of the present invention will become more readily apparent from a better understanding of the preferred embodiments described below with reference to the following drawings, in which.

DETAILED DESCRIPTION OF THE PREFERRED EMBODIMENT

Figure 1:
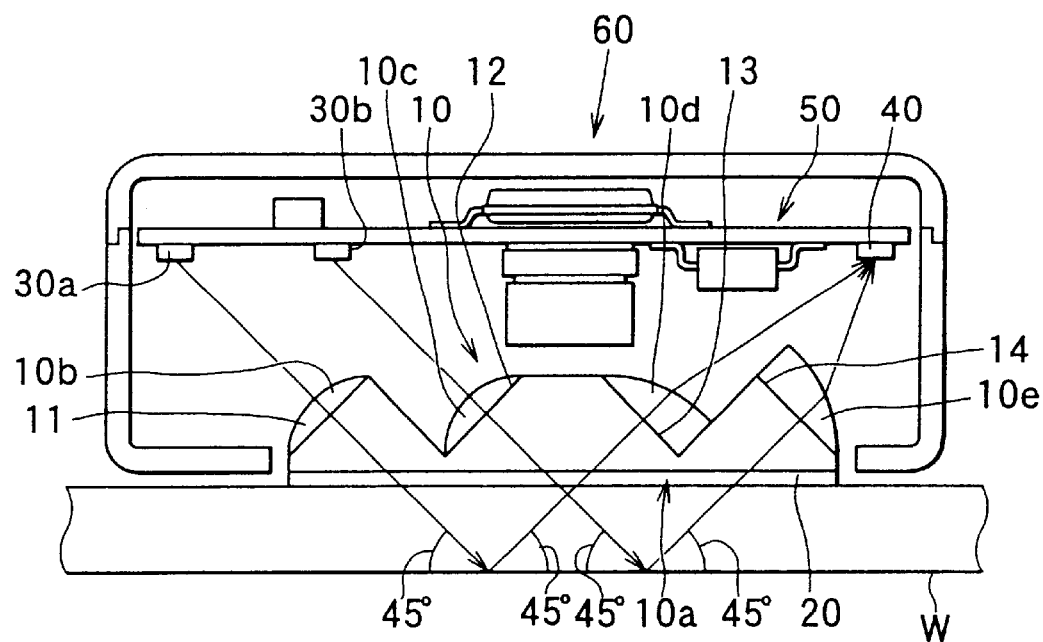
FIG. 1 is a cross-sectional view showing a raindrop sensor attached to a windshield of a vehicle in a preferred embodiment according to the present invention.

The present invention is applied to a vehicle raindrop sensor S shown in FIG. 1 in a preferred embodiment. The raindrop sensor S is adopted to a wiper automatic control device for a wiper that is attached to an exterior wall (reference surface, detection surface) of a windshield W of a vehicle. The wiper automatic control device drive-controls the wiper so that the wiper slidably moves on a wiped region of the exterior wall of the windshield W in accordance with output detected by the raindrop sensor S. The raindrop sensor S is attached to the interior wall corresponding to the wiped region of the windshield W, and optically detects raindrops dropped on the wiped region.

Referring to FIG. 1, the raindrop sensor S has a prism 10 that is attached to the interior wall (corresponding to the wiped region) of the windshield W through a transparent adhesive layer 20. In the present embodiment, the right side and the left side of the raindrop sensor S in FIG. 1 respectively correspond to the right side and the left side of the vehicle.

Figure 2:
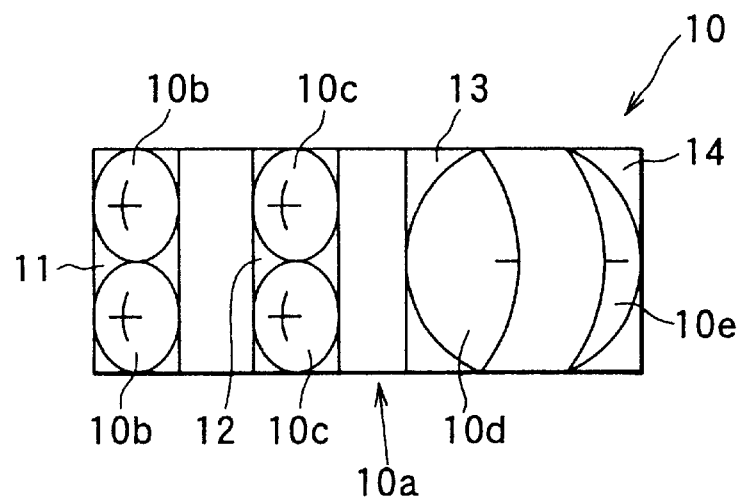
FIG. 2 is a plan view showing a prism of the raindrop sensor.
Figure 3:
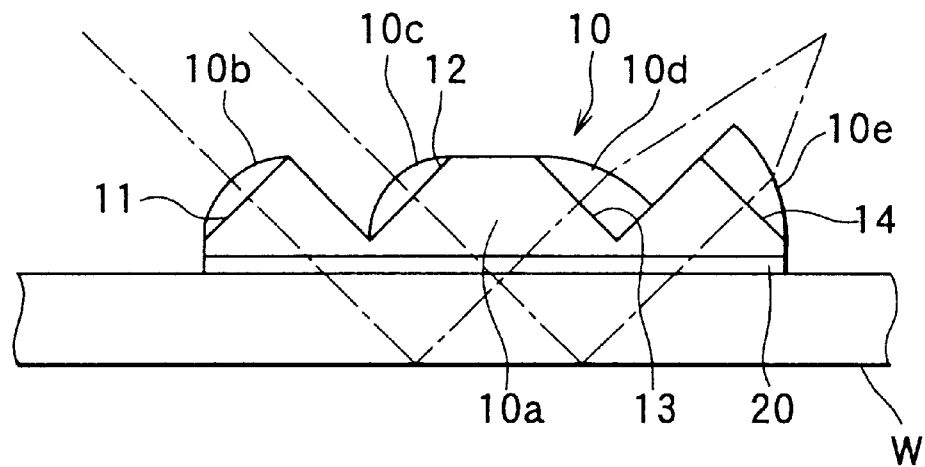
FIG. 3 is a side view showing the prism shown in FIG. 2.
Figure 4:
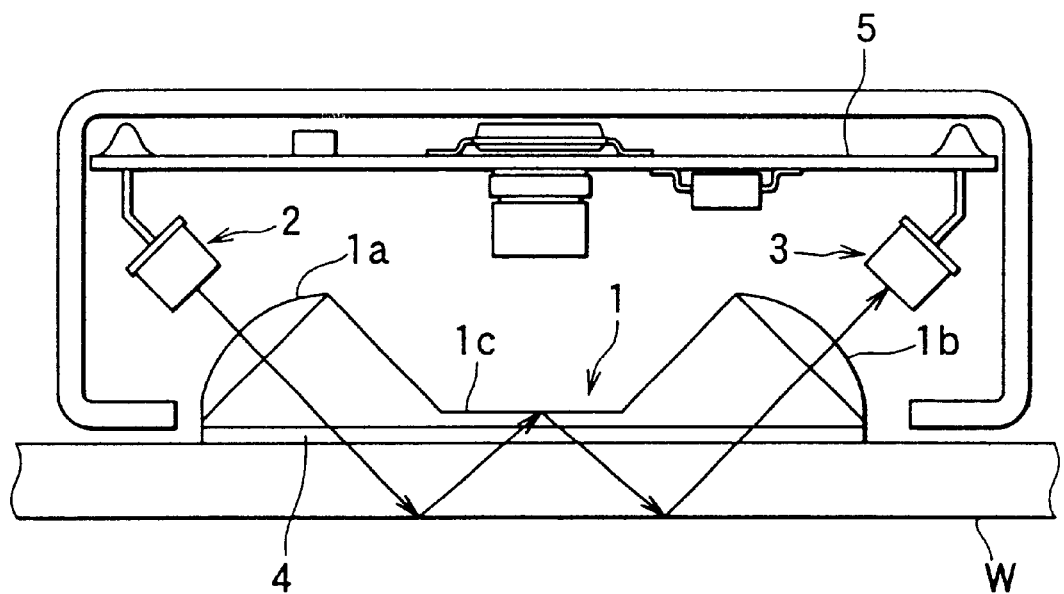
FIG. 4 is a cross-sectional view showing a conventional raindrop sensor attached to a windshield of a vehicle.

The prism 10 is formed from a transparent resin material to have a cross-sectional shape as shown in FIG. 1. As shown in FIGS. 1 to 3, the prism 10 is composed of a prismbody 10a, incidence (incoming radiation) side plano-convex lens portions 10b and 10c, and outgoing radiation side plano-convex lens portions 10d and 10e.

As shown in FIG. 2, two plano-convex portions 10b are arranged on an incidence side inclined surface 11 of the prism body 10a in line, while two plano-convex lens portions 10c are arranged on an incidence side inclined surface 12 of the prism body 10a in line. The inclined surface 12 is provided at the side of the outgoing radiation side of the inclined surface 11 to be parallel with the inclined surface 11. The inclined surfaces 11 and 12 respectively make an angle of approximately 45 degrees with respect to the exterior wall of the windshield W. Accordingly, as shown in FIG. 1, each optical axis of the plano-convex lens portions 10b and 10c forms an angle of approximately 45 degrees with respect to the exterior wall of the windshield W.

The plano-convex lens portion 10d is attached to an outgoing radiation side inclined surface 13 of the prism body 10a, while the plano-convex lens portion 10e is attached to an outgoing radiation side inclined surface 14 of the prism body 10a at the right side of the inclined surface 13 in FIG. 1. The lens portions 10d and 10e are provided by dividing one plano-convex lens into two pieces. That is, the lens portions 10d and 10e can form one plano-convex lens cooperatively when they are matched. The lens portion 10d has a diameter larger than that of each lens portion 10b so that it receives light from both the lens portions 10b. The lens portion 10e has a diameter larger than that of each lens portion 10c, so that it receives light from both the lens portions 10c. The diameter of the lens portion 10d is identical with that of the lens portion 10e.

As shown in FIG. 1, the inclined surfaces 13 and 14 are also respectively formed to make an angle of approximately 45 degrees with respect to the exterior wall of the windshield W. The inclined surface 13 makes an angle of approximately 90 degrees with respect to the inclined surface 11, while the inclined surface 14 makes an angle of approximately 90 degrees with respect to the inclined surface 12. Each optical axis of the plano-convex lens portions 10d, 10e makes an angle of approximately 45 degrees with respect to the exterior wall of the windshield W. Hereinafter, the plano-convex lens portions 10d and 10e are referred to as divided plano-convex lens portions 10d and 10e.

The raindrop sensor S has two light-emitting elements 30a and two light-emitting elements 30b. FIG. 1 shows one of the elements 30a and one of the elements 30b only. Each of the light-emitting elements 30a and 30b is a chip type and surface-mounted type light-emitting element, and bonded to a lower surface of a wiring board 50 directly. Each of the light-emitting elements 30a has a light-emitting axis corresponding to each optical axis of the plano-convex lens portions 10b, and each of the light-emitting elements 30b has a light-emitting axis corresponding to each optical axis of the plano-convex lens portions 10c.

Accordingly, light emitted by each light-emitting element 30a is incident on each plano-convex lens portion 10b along the optical axis. Light incident on the plano-convex lens portion 10b is then incident on the exterior wall of the windshield W after passing through the prism body 10a and the adhesive layer 20. Light from the plano-convex lens portion 10b is then reflected by the exterior wall of the windshield W to enter the divided plano-convex lens portion 10d after passing through the prism body 10a. The divided plano-convex lens portion 10d emits light toward a light-receiving element 40 described later.

Each of the light-emitting elements 30b emits light toward each plano-convex lens portion 10c along the optical axis thereof. The light is then incident on the exterior wall of the windshield W after passing through the prism body 10a and the adhesive layer 20, and reflected by the exterior wall toward the divided plano-convex lens portion 10e. The divided plano-convex lens portion 10 emits the light toward the light-receiving element 40. Incidentally, since each of the divided plano-convex lens portions 10d and 10e refracts light toward the divided surface side there of, each light from the divided plano-convex lens portions 10d and 10e is incident on the light-receiving element 40.

The raindrop sensor has the single light-receiving element 40 that is composed of a chip type and surface-mounted type light-receiving element. The light-receiving element 40 is mounted on the lower surface of the wiring board 50 directly at a position shown in FIG. 1 to receive light from the divided plano-convex lens portions 10d and 10e. Incidentally, in FIG. 1, reference numeral 60 denotes a casing accommodating therein the wiring board 50, the light-emitting elements 30a and 30b, the light-receiving element 40, and the prism 10.

In the present embodiment, light incident on the exterior wall of the windshield W is totally reflected by the exterior wall when no raindrops are attached to the wiped region. If raindrops are attached to the wiped region, the amount of light reflected by the windshield W is reduced.

In the raindrop sensor thus constructed as in the present embodiment, as shown in FIGS. 1 and 2, since the light-emitting elements 30a and 30b are arranged in two lines, the detection region of the sensor can be widened, thereby improving detection accuracy of the sensor.

Also, since the divided plano-convex lens portions 10d and 10e are provided by dividing one plano-convex lens portion into two pieces, the height of the inclined surfaces 13 and 14 holding A the divided plano-convex lens portions 10d and 10e can be decreased in a vertical direction. Consequently, the height of the prism 10 can be decreased. In addition, since each of the light-emitting elements 30a and 30b and the light-receiving element 40 is a surface mounted type element, a projection length of each element from the lower surface of the wiring board 50 is short as compared to a conventional light-emitting or light-receiving element, thereby decreasing the interval between the wiring board 50 and the prism 10.

Also, as described above, since the divided plano-convex lens portions 10d and 10e, which can form one plano-convex lens cooperatively, are respectively attached to the inclined surfaces 13 and 14 as shown in FIG. 2, light from the lens portions 10d and 10e enters the single light-receiving element 40. Thus the number of light-receiving elements can be decreased as compared to that of the light-emitting elements. As a result, the raindrop sensor can be provided with a widened detection region and a compact structure without increasing the number of parts. The plano-convex lens portions may be formed with the prism body 10a integrally. The present invention can be applied not only to raindrop sensors for vehicles but also to raindrop sensors for ships, aircraft, and the like.

While the present invention has been shown and described with reference to the foregoing preferred embodiments, it will be apparent to those skilled in the art that changes in form and detail may be made therein without departing from the scope of the invention as defined in the appended claims.

What is claimed is:

1. A raindrop sensor comprising:

a prism body adapted for attachment to a member having a reference surface, the prism body having first and second incoming radiation side inclined surfaces inclined with respect to the reference surface, and first and second outgoing radiation side inclined surfaces inclined with respect to the reference surface in an opposite direction of the first and second incoming radiation side inclined surfaces, the first and second incoming radiation side inclined surfaces being parallel with each other, the first and second outgoing radiation side inclined surfaces being parallel with each other;

a wiring board provided to face the first and second incoming radiation side inclined surfaces and the first and second outgoing radiation side inclined surfaces of the prism body;

first and second incoming radiation side plano-convex lens portions respectively provided on the first and second incoming radiation side inclined surfaces with respective convex surfaces projecting outwardly;

first and second outgoing radiation side plano-convex lens portions respectively provided on the first and second outgoing radiation side inclined surfaces with respective convex surfaces projecting outwardly;

first and second light-emitting elements provided on the wiring board to face the first and second incoming radiation side plano-convex lens portions, respectively; and a light-receiving element provided on the wiring board to face the first and second outgoing radiation side plano-convex lens portions, wherein:

the first outgoing radiation side plano-convex lens portion and the second outgoing radiation side piano-convex lens portion being complementary parts of a single plano-convex lens divided by a plane, wherein each of the first and second outgoing radiation side plano-convex lens portions has a divided surface defined by the plane;

the divided surface of each of the first and second outgoing radiation side piano-convex lens portions extending parallel to an optical axis of each of the first and second outgoing radiation side plano-convex lens portions;

the divided surface of the first outgoing radiation side plano-convex lens portion facing a first direction, which is perpendicular to the optical axis of each of the first and second outgoing radiation side plano-convex lens portions, and the divided surface of the second outgoing radiation side plano-convex lens portion facing a second direction, which is opposite to the first direction;

light, which internally exits the prism body via each of the first and second outgoing radiation side plano-convex lens portions entering the same light-receiving element; and the second outgoing radiation side plano-convex lens portion being provided at an outgoing radiation side of the first outgoing radiation side plano-convex lens portion with respect to the first and second incoming radiation side plano-convex lens portions so that the divided surface of the second outgoing radiation side plano-convex lens portion faces the divided surface of the first outgoing radiation side plano-convex lens portion.

2. A raindrop sensor as in claim 1, wherein each of the first and second light-emitting elements and the light-receiving element is a surface-mounted element.

3. A raindrop sensor as in claim 1 wherein the first outgoing radiation side plano-convex lens portion is substantially the same size as that of the second outgoing radiation side plano-convex lens portion.

4. A raindrop sensor as in claim 1 wherein a convex surface of each of the first and second outgoing radiation side plano-convex lens portions has a curvature smaller than that of each of the first and second incoming radiation side plano-convex lens portions.

5. A raindrop sensor as in claim 1 wherein:

the divided surface of the first outgoing radiation side plano-convex lens portion extends in a direction perpendicular to the first outgoing radiation side inclined surface of the prism body; and the divided surface of the second outgoing radiation side plano-convex lens portion extends in a direction perpendicular to the second outgoing radiation side inclined surface of the prism body.

6. A raindrop sensor for detecting raindrops on a detection surface, said sensor comprising:

a prism body having a first surface for facing the detection surface to detect raindrops on the detection surface, and a second surface provided at an opposite side of the first surface;

a member facing the second surface of the prism body;

a plurality of light-emitting elements each provided on the member to emit light toward the prism body;

a plurality of first side plano-convex lenses each provided on the second surface of the prism body to receive light from a corresponding one of the plurality of light-emitting elements;

a plurality of second side plano-convex lenses each provided on the second surface of the prism body to receive light passing through a corresponding one of the plurality of first side plano-convex lenses and reflected by the detection surface wherein the second side plano-convex lenses are complementary parts of a single plano-convex lens divided by at least one plane, and each of the second side plano-convex lenses having at least one divided surface, wherein each divided surface is defined by a corresponding one of the at least one plane; and a light-receiving element provided on the member for receiving light from the plurality of second side plano-convex lenses, wherein:

each divided surface of each of the second side plano-convex lenses extends parallel to an optical axis of each of the second side plano-convex lenses;

one of the at least one divided surface of a first one of the second side plano-convex lenses faces a first direction, which is perpendicular to the optical axis of each of the second side plano-convex lenses, and one of the at least one divided surface of a second one of the second side plano-convex lenses, which is located next to one of the at least one divided surface of the first one of the second side plano-convex lenses, faces a second direction, which is opposite to the first direction; and light, which exits each of the second side plano-convex lenses, entering the light-receiving element.

7. A raindrop sensor as in claim 6, wherein:

the second surface of the prism body has a plurality of first side inclined surfaces for holding the plurality of first side plano-convex lenses thereon, and a plurality of second side inclined surfaces for holding the plurality of second side plano-convex lenses thereon, the plurality of first side inclined surfaces being parallel with one another and making a specific angle with the reference surface, the plurality of second side inclined surfaces being parallel with one another and making an angle of substantially 90 degrees with respect the plurality of first side inclined surfaces.

8. A raindrop sensor as in claim 6, wherein each of the plurality of second side plano-convex lenses receives light reflected by the detection surface and refracts the light toward a side of the divided surface thereof so that the refracted light enters the light-receiving element.

9. A raindrop sensor as in claim 6, wherein the light-receiving element is a single element.

10. A raindrop sensor as in claim 6, wherein:

the plurality of second side plano-convex lenses have an assumed optical axis of the one optical lens that can be cooperatively formed by the plurality of second side plano-convex lenses; and the plurality of second side plano-convex lenses are shifted with respect to one another on the prism body in a direction parallel to the assumed optical axis.

* * * * *